United States Patent [19]

Pinol et al.

[11] Patent Number: 5,087,621
[45] Date of Patent: Feb. 11, 1992

[54] SUBSTITUTED AZETIDINYLISOTHIAZOLOPYRIDONE DERIVATIVES, THEIR PREPARATION AND THEIR APPLICATION AS MEDICINAL PRODUCTS

[75] Inventors: Augusto C. Pinol; Jordi F. Constansa; Juan P. Corominas, all of Barcelona, Spain

[73] Assignee: Laboratorios del Dr. Esteve, Barcelona, Spain

[21] Appl. No.: 507,957

[22] Filed: Apr. 11, 1990

[30] Foreign Application Priority Data

Apr. 18, 1989 [FR] France ............... 89 05129

[51] Int. Cl.$^5$ ............... A61K 31/395; C07D 513/02; C07D 513/12
[52] U.S. Cl. ............... 514/210; 514/287; 514/292; 514/293; 546/62; 546/64; 546/83
[58] Field of Search ............... 546/83, 62, 64; 514/293, 210, 286, 292, 282

[56] References Cited

U.S. PATENT DOCUMENTS 4,767,762  8/1988  Chu ............... 546/83

FOREIGN PATENT DOCUMENTS 265092  10/1989  Japan ............... 546/83

OTHER PUBLICATIONS

Chu, Chem. Abst. 107-217616t (1987).
Chu, Chem. Abst. 108-21912n (1988).

Primary Examiner—Cecilia Shen
Attorney, Agent, or Firm—Dressler, Goldsmith, Shore, Sutker & Milnamow, Ltd.

[57] ABSTRACT

The present invention relates to substituted azetidinylisothiazolopyridone derivatives which correspond to the general formula I:

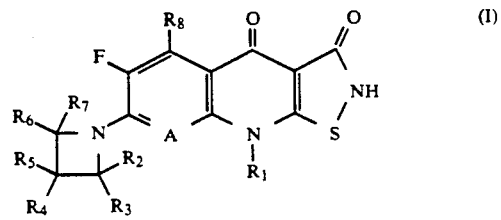

or its tautomeric formula

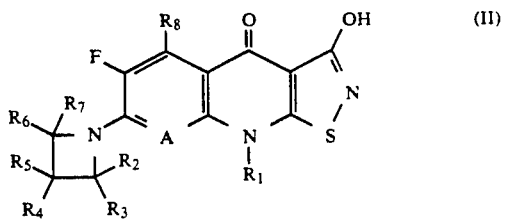

It also relates to a process for preparing them and to their application as a medicinal product.

12 Claims, No Drawings

SUBSTITUTED AZETIDINYLISOTHIAZOLOPYRIDONE DERIVATIVES, THEIR PREPARATION AND THEIR APPLICATION AS MEDICINAL PRODUCTS

The present invention relates to new azetidine derivatives of isothiazolopyridone: 2,3,4,9-tetrahydroisothiazolo[5,4-b]quinoline-3,4-dione, 2,3,4,9-tetrahydroisothiazolo[5,4-b][1,8]naphthyridine-3,4-dione and 1,2,8,9-tetrahydro-7H-isothiazolo[4',5':5,6]pyrido[1,2,3-de]benzoxazine-7,8-dione; therapeutically acceptable salts of these compounds, a process for preparing them and also their application as medicinal products.

The compounds which are the subject of the present invention may be used in the pharmaceutical industry as intermediates and for the preparation of medicinal products.

Isothiazolonaphthyridines and isothiazoloquinolines were already known, for example in the Patent Eur. Pat. Appl. EP 227,088, as were isothiazolopyridobenzoxazines, for example in the Patent Eur. Pat. Appl. EP 228,661, but in none of these cases have examples been found with azetidines as substituents.

We have now discovered that the new azetidine derivatives of isothiazolonaphthyridine, isothiazoloquinoline and isothiazolopyridobenzoxazines which form the subject of the present invention possess very good antimicrobial activity.

The compounds which are the subject of the present invention correspond to the general formula I

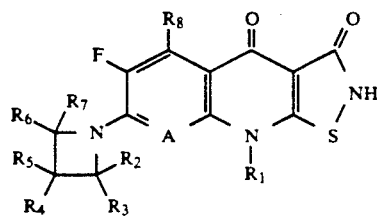

which may also be written in its tautomeric formula II

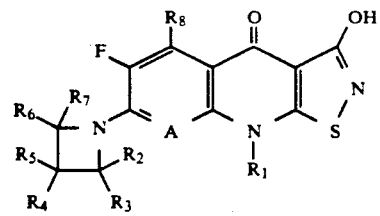

in which formulae A represents a nitrogen atom, or alternatively a carbon atom with a hydrogen atom attached (C—H), or alternatively a carbon atom with a halogen attached (C—X), and in this case X represents a bromine, chlorine or fluorine atom, $R_1$ represents a lower alkyl or cycloalkyl radical, a lower haloalkyl radical, an aryl radical or an aryl radical substituted, in particular, with one or more fluorine atom(s), $R_2$ and $R_7$, which may be the same or different, represent a hydrogen atom or a lower alkyl radical, $R_3$, $R_5$ and $R_6$, which may be the same or different, represent a hydrogen atom, a lower alkyl radical, an aminoalkyl radical, an alkylamino radical or an alkylaminoalkyl radical, $R_4$ represents a hydrogen atom, a lower alkyl radical, a hydroxyl radical, an amino radical, an aminoalkyl radical, an alkylamino radical, a dialkylamino radical, a nitrogenous heterocyclic radical which can be a three- to six-membered ring, an alkylaminoalkyl radical, an alkylcarboxamido radical, and it being possible in this case for the alkyl radical to be substituted with one or more halogens, an arysulfonyloxy radical, an alkylsulfonyloxy radical, a carboxamido radical which can be substituted or otherwise on the nitrogen, or a cyano radical, $R_8$ represents a hydrogen atom, a nitro radical or an amino or substituted amino radical, A and $R_1$ together can form a link represented by a group C—CH$_2$—CH$_2$—CHR$_9$— or C—O—CH$_2$—CHR$_9$— in which groups R$_9$ represents a hydrogen atom or a lower alkyl radical, and in the latter case a chiral centre with an "R" or "S" configuration.

Depending on the number, nature and relative position of the substituents, the azetidine substituents can have up to three chiral centres, each of them with an "R" or "S" configuration.

The stereochemistry of the products which are the subject of the present invention is determined by that of the starting materials. By selection of the stereoisomerism of each of the starting materials, all the possible stereoisomers can be obtained, and in the case where the reaction product is a mixture of stereoisomers, the components may be separated and their configuration established by well-known procedures.

The new derivatives of general formula I may be prepared, according to the invention, according to the following method:

by the reaction of a compound of general formula III

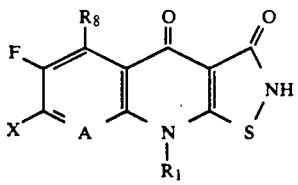

in which A, $R_1$ and $R_8$ have the meanings stated above and X represents a halogen atom, preferably a chlorine or a fluorine, with an azetidine of general formula IV

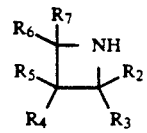

in which $R_2$, $R_3$, $R_4$, $R_5$, $R_6$ and $R_7$ have the meanings stated above.

The reaction is performed in the presence of an appropriate solvent, for example dimethyl sulfoxide, dimethylformamide, pyridine, trialkylamines such as triethylamine, methylene chloride, chloroform, acetonitrile or alternatively, ethers such as tetrahydrofuran or dioxane, or mixtures of these solvents.

The most appropriate temperatures vary between room temperature and the refluxing temperature of the solvent, and the reaction time is between 1 hour and 24 hours.

The heterocyclic compounds of general formula III which can be used as starting materials for preparing the compounds of the invention are compounds described, for example, in D. T. W. Chu, P. B. Fernandes, A. K. Claiborne, L. Shen and A. G. Pernet, *Drugs Exptl. Chim. Res.* 14(6), 379, (1988).

Furthermore, the compounds of general formula IV, which constitute the other starting materials for the preparation of the compounds of the invention according to the general formula I, are known or else are synthesized as, for example, in A. G. Anderson and R. Lok, *J. Org. Chem.* 1972, 37, 3953 or alternatively in R. H. Higgins and N. H. Cromwell, *J. Heterocycl. Chem.*, 1971, 8, 1059 and also in N. H. Cromwell and B. Phillips, *Chem. Revs.*, 1979, 79, 331.

Depending on the number, nature and relative position of the substituents, the azetidines of general formula IV can have up to three chiral centres, and the different stereoisomers may be obtained either by asymmetric synthesis or by various types of separations, according to procedures known in organic chemistry.

The compounds of general formula I and their physiologically acceptable salts, such as the salts with inorganic acids such as the hydrochlorides, or with organic acids such as the toluenesulfonates or methylsulfonates, are preferably administered in the form of pharmaceutical compositions.

In the examples which follow, the preparation of new derivatives according to the invention is described. Some modes of use will also be described.

The examples below, given simply by way of illustration, are not, however, in any way to limit the scope of the invention.

EXAMPLE 1

Preparation of 9-cyclopropyl-6-fluoro-7-(3-amino-1-azetidinyl)-2,3,4,9-tetrahydroisothiazolo[5,4-b]quinoline-3,4-dione.

A mixture of 140 mg (0.475 mmol) of 9-cyclopropyl-6,7-difluoro-2,3,4,9-tetrahydroisothiazolo[5,4-b]quinoline-3,4-dione, 300 mg (2 mmol) of 3-aminoazetidine dihydrochloride and 1 ml of triethylamine in 5 ml of pyridine and 5 ml of dimethyl sulfoxide is kept refluxing for 2 hours. The mixture is filtered, the product is washed with water and ethanol and dried in the heated state and 102 mg of 9-cyclopropyl-6-fluoro-7-(3-amino-1-azetidinyl)-2,3,4,9-tetrahydroisothiazolo[5,4-b]quinoline-3,4,-dione, melting point 270° C. (d), are obtained.

Spectroscopic data: $^1$H NMR, $\delta$, [DMSO-d$_6$/TFAA]: 8.42 (b, 2H); 7.60 (d, 1H, J=13 Hz); 6.79 (d, 1H, J=7 Hz); 4.16 (m, 4H); 3.42 (m, 2H); 1.20 (m, 4H).

IR (KBr): 1629, 1602, 1492 cm$^{-1}$.

EXAMPLE 2

Preparation of 9-cyclopropyl-6-fluoro-7-(3-methylamino-1-azetidinyl)-2,3,4,9-tetrahydroisothiazolo[5,4-b]quinoline-3,4-dione.

A mixture of 500 mg (1.7 mmol) of 9-cyclopropyl-6,7-difluoro-2,3,4,9-tetrahydroisothiazolo[5,4-b]quinoline-3,4-dione, 750 mg (3.4 mmol) of 3-[N-(methyl)trifluoroacetamido]azetidine hydrochloride and 1.2 ml of triethylamine in 10 ml of pyridine and 10 ml of dimethyl sulfoxide is kept refluxing for 1.5 hours. The mixture is filtered, the product is washed with water and ethanol and dried in the heated state and 430 mg of 9-cyclopropyl-6-fluoro-7-{3-[N-(methyl)trifluoroacetamido]-1-azetidinyl}-2,3,4,9-tetrahydroisothiazolo[5,4-b]quinoline-3,4-dione, melting point 284°-290° C., are obtained, which product is then hydrolyzed by heating it with 10% sodium hydroxide for 2 hours. The mixture is filtered, the product is washed with water and ethanol and dried in the heated state and 340 mg of 9-cyclopropyl-6-fluoro-7-(3-methylamino-1-azetidinyl)-2,3,4,9-tetrahydroisothiazolo[5,4-b]quinoline-3,4-dione, melting point 270° C. (d), are obtained.

Spectroscopic data: $^1$H NMR, $\delta$, [DMSO-d$_6$/TFAA]: 9.22 (b, 2H); 7.71 (d, 1H, J=13 Hz); 6.81 (d, 1H, J=6 Hz); 4.35 (m, 4H); 3.45 (m, 1H); 2.64 (s, 3H); 1.29 (m, 4H).

IR (KBr): 1629, 1588, 1497, 1431 cm$^{-1}$.

EXAMPLE 3

Preparation of 9-cyclopropyl-6-fluoro-7-(3-dimethylamino-1-azetidinyl)-2,3,4,9-tetrahydroisothiazolo[5,4-b]quinoline-3,4-dione.

A mixture of 150 mg (0.51 mmol) of 9-cyclopropyl-6,7-difluoro-2,3,4,9-tetrahydroisothiazolo[5,4-b]quinoline-3,4-dione, 250 mg (1.45 mmol) of 3-dimethylaminoazetidine dihydrochloride and 1 ml of triethylamine in 5 ml of pyridine and 5 ml of dimethyl sulfoxide is kept refluxing for 2 hours. The pyridine and triethylamine are evaporated off under vacuum and, after cooling, the mixture is filtered, the product is washed with water and ethanol and dried in the heated state and 126 mg of 9-cyclopropyl-6-fluoro-7-(3-dimethylamino-1-azetidinyl)-2,3,4,9-tetrahydroisothiazolo[5,4-b]quinoline-3,4-dione, melting point 287° C. (d), are obtained.

Spectroscopic data: $^1$H HMR, $\delta$, [DMSO-d$_6$/TFAA]: 7.70 (d, 1H, J=13 Hz); 6.77 (d, 1H, J=7 Hz); 4.34 (m, 4H); 3.43 (m, 2H); 2.83 (s, 6H); 1.20 (m, 4H).

IR (KBr): 1640, 1612, 1501 cm$^{-1}$.

EXAMPLE 5

Preparation of 9-cyclopropyl-6-fluoro-7-(trans-3-amino-2-methyl-1-azetidinyl)-2,3,4,9-tetrahydroisothiazolo[5,4-b]quinoline-3,4-dione.

A mixture of 150 mg (0.51 mmol) of 9-cyclopropyl-6,7-difluoro-2,3,4,9-tetrahydroisothiazolo[5,4-b]quinoline-3,4-dione, 300 mg (1.9 mmol) of trans-3-amino-2-methylazetidine dihydrochloride and 1 ml of triethylamine in 5 ml of pyridine and 5 ml of dimethyl sulfoxide is kept refluxing for 2 hours. The mixture is filtered, the product is washed with water and ethanol and dried in the heated state and 105 mg of 9-cyclopropyl-6-fluoro-7-(trans-3-amino-2-methyl-1-azetidinyl)-2,3,4,9-tetrahydroisothiazolo[5,4-b]quinoline-3,4-dione, melting point 264°-7° C., are obtained.

Spectroscopic data: $^1$H NMR, $\delta$, [DMSO-d$_6$/TFAA]: 8.34 (b, 2H); 7.75 (d, 1H, J=13 Hz); 6.89 (d, 1H, J=7 Hz); 4.44 (m, 2H); 3.88 (m, 1H); 3.44 (m, 2H); 1.52 (d, 3H); 1.20 (m, 4H).

IR (KBr): 1628, 1592, 1486 cm$^{-1}$.

EXAMPLE 9

Preparation of 9-cyclopropyl-6-fluoro-7-(3-amino-3-methyl-1-azetidinyl)-2,3,4,9-tetrahydroisothiazolo[5,4-b]quinoline-3,4-dione.

A mixture of 90 mg (0.3 mmol) of 9-cyclopropyl 6,7-difluoro-2,3,4,9-tetrahydroisothiazolo[5,4-b]quinoline-3,4-dione, 200 mg (1.25 mmol) of 3-amino-3-methylazetidine dihydrochloride and 1 ml of triethylamine in 5 ml of pyridine and 5 ml of dimethyl sulfoxide is kept refluxing for 2 hours. The mixture is filtered, the product is washed with water and ethanol and dried in the heated state and 70 mg of 9-cyclopropyl-6-fluoro-7-

(3-amino-3-methyl-1-azetidinyl)-2,3,4,9-tetrahydroisothiazolo[5,4-b]quinoline-3,4-dione, melting point 297°-302° C., are obtained.

Spectroscopic data: $^1$H NMR, δ, [DMSO-d$_6$/TFAA]: 8.50 (b, 2H); 7.72 (d, 1H, J=13 Hz); 6.79 (d, 1H, J=7 Hz); 4.21 (m, 4H); 3.45 (m, 1H); 1.64 (s, 3H); 1.25 (m, 4H).

IR (KBr): 1629, 1592, 1492 cm$^{-1}$.

Preparation of 9-cyclopropyl-6-fluoro-7-(3-amino-3-methyl-1-azetidinyl)-2,3,4,9-tetrahydroisothiazolo[5,4-b]quinoline-3,4-dione methylsulfonate.

60 mg (0.17 mmol) of 9-cyclopropyl-6-fluoro-7-(3-amino-3-methyl-1-azetidinyl)-2,3,4,9-tetrahydroisothiazolo[5,4-b]quinoline-3,4-dione are suspended in 10 ml of methanol and an excess of methylsulfonic acid is added. The mixture is stirred for 15 minutes and filtered, the product is washed with methanol and dried in the heated state and 55 mg of the salt indicated above, melting point 223°-227° C., are obtained.

Spectroscopic data: $^1$H NMR, δ, [DMSO-d$_6$/TFAA]: 8.44 (b, 2H); 7.62 (d, 1H, J=13 Hz); 6.72 (d, 1H, J=7 Hz); 4.16 (m, 4H); 3.43 (m, 1H); 2.50 (s, 3H); 1.60 (s, 3H); 1.20 (m, 4H).

IR (KBr): 1638, 1617, 1498 cm$^{-1}$.

EXAMPLE 10

Preparation of 9-cyclopropyl-6-fluoro-7-(3-methylamino-3-methyl-1-azetidinyl)-2,3,4,9-tetrahydroisothiazolo[5,4-b]quinoline-3,4-dione.

By a procedure completely analogous to that described in Example 2, 9-cyclopropyl-6-fluoro-7-{3-[N-(methyl)trifluoroacetamido]-3-methyl-1-azetidinyl}-2,3,4,9-tetrahydroisothiazolo[5,4-b]quinoline-3,4-dione, melting point 286°-290° C., is obtained, which product is hydrolyzed by heating it with 10% sodium hydroxide for 2 hours; 9-cyclopropyl-6-fluoro-7-(3-methylamino-3-methyl-1-azetidinyl)-2,3,4,9-tetrahydroisothiazolo[5,4-b]quinoline-3,4-dione, melting point 300° C., is obtained.

Spectroscopic data: $^1$H NMR, δ, [DMSO-d$_6$/TFAA]: 9.39 (b, 2H); 7.80 (d, 1H, J=13 Hz); 6.90 (d, 1H, J=6 Hz); 4.28 (m, 4H); 3.46 (m, 1H); 2.70 (s, 3H); 1.69 (s, 3H); 1.22 (m, 4H).

IR (KBr): 1625, 1597, 1495, 1474, 1428, 1385 cm$^{-1}$.

EXAMPLE 22

Preparation of 9-cyclopropyl-6-fluoro-7-(3-ethylamino-1-azetidinyl)-2,3,4,9-tetrahydroisothiazolo[5,4-b]quinoline-3,4-dione.

By a procedure completely analogous to that described in Example 2, 9-cyclopropyl-6-fluoro-7-{3-[N-(ethyl)trifluoroacetamido]-1-azetidinyl}-2,3,4,9-tetrahydroisothiazolo[5,4-b]quinoline-3,4-dione, melting point 256°-259° C., is obtained, which product is hydrolyzed by heating it with 10% sodium hydroxide for 2 hours; 9-cyclopropyl-6-fluoro-7-(3-ethylamino-1-azetidinyl)-2,3,4,9-tetrahydroisothiazolo[5,4-b]quinoline-3,4-dione, melting point 231°-236° C., is obtained.

Spectroscopic data: $^1$H NMR, δ, [DMSO-d$_6$/TFAA]: 9.39 (b, 2H); 7.69 (d, 1H, J=13 Hz); 6.80 (d, 1H, J=6 Hz); 4.29 (m, 4H); 3.43 (m, 1H); 3.03 (m, 2H); 1.31 (m, 7H).

IR (KBr): 1628, 1601, 1492, 1472, 1422 cm$^{-1}$.

EXAMPLE 29

Preparation of 9-cyclopropyl-6,8-difluoro-7-(trans-3-amino-2-methyl-1-azetidinyl)-2,3,4,9-tetrahydroisothiazolo[5,4-b]quinoline-3,4-dione.

A mixture of 125 mg (0.4 mmol) of 9-cyclopropyl6,7,8-trifluoro-2,3,4,9-tetrahydroisothiazolo[5,4-b]quinoline-3,4-dione, 128 mg (0.8 mmol) of trans-2-methyl3-aminoazetidine dihydrochldoride and 0.34 ml of triethylamine in 4 ml of pyridine and 4 ml of dimethyl sulfoxide is kept refluxing for 2 hours. The mixture is filtered, the product is washed with water and ethanol and dried in the heated state and 93 mg of 9-cyclopropyl-6,8-difluoro-7-(trans-3-amino-2-methyl-1-azetidinyl)-2,3,4,9-tetrahydroisothiazolo[5,4-b]quinoline-3,4-dione, melting point 268°-270° C., are obtained.

Spectroscopic data: $^1$H NMR, δ, [DMSO-d$_6$/TFAA]: 8.35 (b, 3H); 7.66 (d, 1H, J=13 Hz); 4.70 (m, 2H); 4.10 (m, 1H); 3.78 (m, 2H); 1.53 (d, 3H, J=6 Hz); 1.15 (m, 4H).

IR (KBr): 1623, 1608, 1605, 1465, 1424 cm$^{-1}$.

EXAMPLE 33

Preparation of 9-cyclopropyl-6,8-difluoro-7-(3-amino-3-methyl-1-azetidinyl)-2,3,4,9-tetrahydroisothiazolo[5,4-b]quinoline-3,4-dione.

A mixture of 250 mg (0.8 mmol) of 9-cyclopropyl-6,7,8-trifluoro-2,3,4,9-tetrahydroisothiazolo[5,4-b]quinoline-3,4-dione, 255 mg (1.6 mmol) of 3-methyl-3-aminoazetidine dihydrochloride and 0.6 ml of triethylamine in 10 ml of pyridine is kept refluxing for 2 hours, the mixture is evaporated under vacuum, a mixture of ethanol with water is added, the resulting mixture is filtered and the product is washed. 0.225 g of 9-cyclopropyl-6,8-difluoro-7-(3-amino-3-methyl-1-azetidinyl)-2,3,4,9-tetrahydroisothiazolo[5,4-b]quinoline-3,4-dione, melting point 294°-300° C., is thereby obtained.

Spectroscopic data: IR (KBr): 1630, 1602, 1469 cm$^{-1}$.

Preparation of 9-cyclopropyl-6,8-difluoro-7-(3-amino-3-methyl-1-azetidinyl)-2,3,4,9-tetrahydroisothiazolo[5,4-b]quinoline-3,4-dione methylsulfonate.

120 mg (0.32 mmol) of 9-cyclopropyl-6,8-difluoro-7-(3-amino-3-methyl-1-azetidinyl)-2,3,4,9-tetrahydroisothiazolo[5,4-b]quinoline-3,4-dione are suspended in 10 ml of methanol and an excess of methylsulfonic acid is added. The mixture is stirred for 15 minutes and filtered, the product is washed with methanol and dried in the heated state and 120 mg of the salt indicated above, melting point 248°-253° C., are obtained.

Spectroscopic data: $^1$H NMR, δ, [DMSO-d$_6$/TFAA]: 8.40 (b, 2H); 7.62 (d, 1H, J=12 Hz); 4.35 (m, 4H); 3.70 (m, 1H); 2.50 (s, 3H); 1.55 (s, 1H); 1.07 (m, 4H).

IR (KBr): 1648, 1619, 1468 cm$^{-1}$.

Using 9-cyclopropyl-6-fluoro-2,3,4,9-tetrahydroisothiazolo[5,4-b]quinoline-3,4-dione as a starting material, the products of Examples 1 to 24 (Table I) may be obtained by the same procedure as in Examples 1, 3 and 5; using 9-cyclopropyl-6,7-difluoro-2,3,4,9-tetrahydroisothiazolo[5,4-b][1,8]quinoline-3,4-dione as a starting material, the products of Examples 25 to 48 (Table I) may be obtained by the same procedure as in Example 33; using 9-cyclopropyl-6,7-difluoro-2,3,4,9-tetrahydroisothiazolo[5,4-b][1,8]naphthyridine-3,4-dione as a starting material, the products of Examples 49 to 72 (Table I) may be obtained by the same procedure as in Example 5; and using 1-methyl-4,5-difluoro-1,2,8,9-tetrahydro-7H-isothiazolo[4',5':5,6]pyrido[1,2,3-de][1,4-]benzoxazine-7,8-dione as a starting material, the products of Examples 73 to 96 may be obtained by the same procedure as in Example 5.

TABLE I

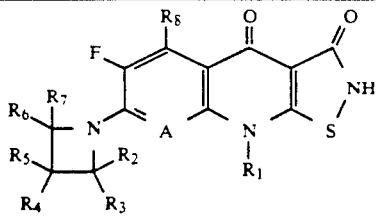

| Example | A | R₁ | R₂ | R₃ | R₄ | R₅ | R₆ | R₇ | R₈ | FORMULA |
|---|---|---|---|---|---|---|---|---|---|---|
| 1 | CH | ▷ | H | H | H₂N | H | H | H | H | $C_{16}H_{15}FN_4O_2S$ |
| 2 | CH | ▷ | H | H | MeNH | H | H | H | H | $C_{17}H_{17}FN_4O_2S$ |
| 3 | CH | ▷ | H | H | Me₂N | H | H | H | H | $C_{17}H_{19}FN_4O_4S$ |
| 4 | CH | ▷ | H | H | HO | H | H | H | H | $C_{16}H_{14}FN_3O_3S$ |
| 5 | CH | ▷ | H | H | H₂N | H | Me | H | H | $C_{17}H_{17}FN_4O_2S$ |
| 6 | CH | ▷ | H | H | MeNH | H | Me | H | H | $C_{18}H_{19}FN_4O_2S$ |
| 7 | CH | ▷ | H | H | Me₂N | H | Me | H | H | $C_{19}H_{21}FN_4O_2S$ |
| 8 | CH | ▷ | H | H | HO | H | Me | H | H | $C_{17}H_{16}FN_3O_3S$ |
| 9 | CH | ▷ | H | H | H₂N | Me | H | H | H | $C_{17}H_{17}FN_4O_2S$ |
| 10 | CH | ▷ | H | H | MeNH | Me | H | H | H | $C_{18}H_{19}FN_4O_2S$ |
| 11 | CH | ▷ | H | H | Me₂N | Me | H | H | H | $C_{19}H_{21}FN_4O_2S$ |
| 12 | CH | ▷ | H | H | HO | Me | H | H | H | $C_{17}H_{16}FN_3O_3S$ |
| 13 | CH | ▷ | H | Me | H₂N | H | Me | H | H | $C_{18}H_{19}FN_4O_2S$ |
| 14 | CH | ▷ | H | Me | MeNH | H | Me | H | H | $C_{19}H_{21}FN_4O_2S$ |
| 15 | CH | ▷ | H | Me | Me₂N | H | Me | H | H | $C_{20}H_{23}FN_4O_2S$ |
| 16 | CH | ▷ | H | Me | HO | H | Me | H | H | $C_{16}H_{18}FN_3O_3S$ |
| 17 | CH | ▷ | H | Me | H₂N | Me | H | H | H | $C_{18}H_{19}FN_4O_2S$ |

TABLE I-continued

| | | | $R_8$ | $R_2$ | $R_3$ | $R_1$ | $R_4$ | $R_5$ | $R_6$ | $R_7$ | |
|---|---|---|---|---|---|---|---|---|---|---|---|
| 18 | CH | △ | H | Me | MeNH | Me | H | H | H | | $C_{20}H_{23}FN_4O_2S$ |
| 19 | CH | △ | H | Me | $Me_2N$ | Me | H | H | H | | $C_{20}H_{23}FN_4O_2S$ |
| 20 | CH | △ | H | Me | HO | Me | H | H | H | | $C_{18}H_{18}FN_3O_3S$ |
| 21 | CH | △ | H | H | $H_2NCH_2$ | H | H | H | H | | $C_{17}H_{17}FN_4O_2S$ |
| 22 | CH | △ | H | H | EtNH | H | H | H | H | | $C_{19}H_{22}FN_4O_2S$ |
| 23 | CH | △ | H | H | $H_2NCH_2$ | Me | H | H | H | | $C_{18}H_{19}FN_4O_2S$ |
| 24 | CH | △ | H | H | $H_2NCH_2$ | H | Me | H | H | | $C_{18}H_{19}FN_4O_2S$ |
| 25 | CF | △ | H | H | $H_2N$ | H | H | H | H | | $C_{16}H_{14}F_2N_4O_2S$ |
| 26 | CF | △ | H | H | MeNH | H | H | H | H | | $C_{17}H_{16}F_2N_4O_2S$ |
| 27 | CF | △ | H | H | $Me_2N$ | H | H | H | H | | $C_{18}H_{18}F_2N_4O_2S$ |
| 28 | CF | △ | H | H | HO | H | H | H | H | | $C_{16}H_{13}F_2N_3O_3S$ |
| 29 | CF | △ | H | H | $H_2N$ | H | Me | H | H | | $C_{17}H_{16}F_2N_4O_2S$ |
| 30 | CF | △ | H | H | MeNH | H | Me | H | H | | $C_{18}H_{18}F_2N_4O_2S$ |
| 31 | CF | △ | H | H | $Me_2N$ | H | Me | H | H | | $C_{19}H_{20}F_2N_4O_2S$ |
| 32 | CF | △ | H | H | HO | H | Me | H | H | | $C_{17}H_{15}F_2N_3O_3S$ |
| 33 | CF | △ | H | H | $H_2N$ | Me | H | H | H | | $C_{17}H_{16}F_2N_4O_2S$ |
| 34 | CF | △ | H | H | MeNH | Me | H | H | H | | $C_{18}H_{18}F_2N_4O_2S$ |
| 35 | CF | △ | H | H | $Me_2N$ | Me | H | H | H | | $C_{19}H_{20}F_2N_4O_2S$ |

TABLE I-continued

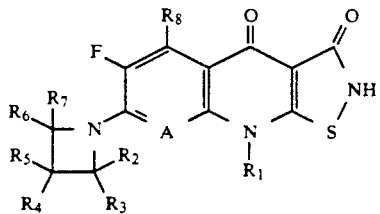

| | | | $R_2$ | $R_3$ | $R_4 R_5$ | $R_6$ | $R_7$ | $R_8$ | |
|---|---|---|---|---|---|---|---|---|---|
| 36 | CF | △ | H | H | HO | Me | H | H | $C_{17}H_{15}F_2N_3O_3S$ |
| 37 | CF | △ | H | Me | $H_2N$ | H | Me | H | $C_{18}H_{18}F_2N_4O_2S$ |
| 38 | CF | △ | H | Me | MeNH | H | Me | H | $C_{19}H_{20}F_2N_4O_2S$ |
| 39 | CF | △ | H | Me | $Me_2N$ | H | Me | H | $C_{20}H_{22}F_2N_4O_2S$ |
| 40 | CF | △ | H | Me | HO | H | Me | H | $C_{18}H_{17}F_2N_3O_3S$ |
| 41 | CF | △ | H | Me | $H_2N$ | Me | H | H | $C_{18}H_{18}F_2N_4O_2S$ |
| 42 | CF | △ | H | Me | MeNH | Me | H | H | $C_{19}H_{20}F_2N_4O_2S$ |
| 43 | CF | △ | H | Me | $Me_2N$ | Me | H | H | $C_{20}H_{22}F_2N_4O_2S$ |
| 44 | CF | △ | H | Me | HO | Me | H | H | $C_{18}H_{17}F_2N_3O_3S$ |
| 45 | CF | △ | H | H | $H_2NCH_2$ | H | H | H | $C_{17}H_{16}F_2N_4O_2S$ |
| 46 | CF | △ | H | H | $EtNHCH_2$ | H | H | H | $C_{19}H_{21}F_2N_4O_2S$ |
| 47 | CF | △ | H | H | $H_2NCH_2$ | Me | H | H | $C_{18}H_{18}F_2N_4O_2S$ |
| 48 | CF | △ | H | H | $H_2NCH_2$ | H | Me | H | $C_{18}H_{18}F_2N_4O_2S$ |
| 49 | N | △ | H | H | $H_2N$ | H | H | H | $C_{15}H_{14}FN_5O_2S$ |
| 50 | N | △ | H | H | MeNH | H | H | H | $C_{16}H_{16}FN_5O_2S$ |
| 51 | N | △ | H | H | $Me_2N$ | H | H | H | $C_{17}H_{18}FN_5O_2S$ |
| 52 | N | △ | H | H | HO | H | H | H | $C_{15}H_{13}FN_4O_3S$ |

TABLE I-continued

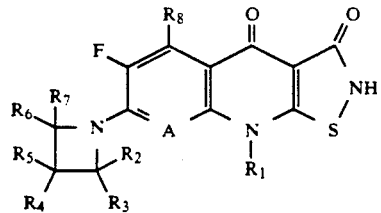

| # | A | R | R₂ | R₃ | R₈ | R₁ | R₆ | R₇ | Formula |
|---|---|---|---|---|---|---|---|---|---|
| 53 | N | ▷ | H | H | H₂N | H | Me | H | H | C₁₆H₁₆FN₅O₂S |
| 54 | N | ▷ | H | H | MeNH | H | Me | H | H | C₁₇H₁₈FN₅O₂S |
| 55 | N | ▷ | H | H | Me₂N | H | Me | H | H | C₁₈H₂₀FN₅O₂S |
| 56 | N | ▷ | H | H | HO | H | Me | H | H | C₁₆H₁₅FN₄O₃S |
| 57 | N | ▷ | H | H | H₂N | Me | H | H | H | C₁₆H₁₆FN₅O₂S |
| 58 | N | ▷ | H | H | MeNH | Me | H | H | H | C₁₇H₁₈FN₅O₂S |
| 59 | N | ▷ | H | H | Me₂N | Me | H | H | H | C₁₈H₂₀FN₅O₂S |
| 60 | N | ▷ | H | H | HO | Me | H | H | H | C₁₆H₁₅FN₄O₃S |
| 61 | N | ▷ | H | Me | H₂N | H | Me | H | H | C₁₇H₁₈FN₅O₂S |
| 62 | N | ▷ | H | Me | MeNH | H | Me | H | H | C₁₈H₂₀FN₅O₂S |
| 63 | N | ▷ | H | Me | Me₂N | H | Me | H | H | C₁₉H₂₂FN₅O₂S |
| 64 | N | ▷ | H | Me | HO | H | Me | H | H | C₁₇H₁₇FN₄O₃S |
| 65 | N | ▷ | H | Me | H₂N | Me | H | H | H | C₁₇H₁₈FN₅O₂S |
| 66 | N | ▷ | H | Me | MeNH | Me | H | H | H | C₁₈H₂₀FN₅O₂S |
| 67 | N | ▷ | H | Me | Me₂N | Me | H | H | H | C₁₉H₂₂FN₅O₂S |
| 68 | N | ▷ | H | Me | HO | Me | H | H | H | C₁₇H₁₇FN₄O₃S |
| 69 | N | ▷ | H | H | H₂NCH₂ | H | H | H | H | C₁₆H₁₆FN₅O₂S |
| 70 | N | ▷ | H | H | EtNHCH₂ | H | H | H | H | C₁₈H₂₁FN₅O₂S |

TABLE I-continued

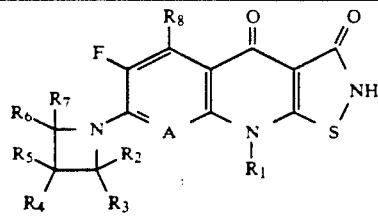

| Example | A—R$_1$ | R$_2$ | R$_3$ | R$_4$ | R$_5$ | R$_6$ | R$_7$ | R$_8$ | FORMULA |
|---|---|---|---|---|---|---|---|---|---|
| 71 | N—▷ | H | H | H$_2$NCH$_2$ | Me | H | H | H | C$_{17}$H$_{18}$FN$_5$O$_2$S |
| 72 | N—▷ | H | H | H$_2$NCH$_2$ | H | Me | H | H | C$_{17}$H$_{18}$FN$_5$O$_2$S |
| 73 | C—O—CH$_2$—CH(CH$_3$)— | H | H | H$_2$N | H | H | H | H | C$_{16}$H$_{15}$FN$_4$O$_3$S |
| 74 | C—O—CH$_2$—CH(CH$_3$)— | H | H | MeNH | H | H | H | H | C$_{17}$H$_{17}$FN$_4$O$_3$S |
| 75 | C—O—CH$_2$—CH(CH$_3$)— | H | H | Me$_2$N | H | H | H | H | C$_{18}$H$_{19}$FN$_4$O$_3$S |
| 76 | C—O—CH$_2$—CH(CH$_3$)— | H | H | HO | H | H | H | H | C$_{16}$H$_{14}$FN$_3$O$_2$S |
| 77 | C—O—CH$_2$—CH(CH$_3$)— | H | H | H$_2$N | H | Me | H | H | C$_{17}$H$_{17}$FN$_4$O$_3$S |
| 78 | C—O—CH$_2$—CH(CH$_3$)— | H | H | MeNH | H | Me | H | H | C$_{18}$H$_{19}$FN$_4$O$_3$S |
| 79 | C—O—CH$_2$—CH(CH$_3$)— | H | H | Me$_2$N | H | Me | H | H | C$_{19}$H$_{21}$FN$_4$O$_3$S |
| 80 | C—O—CH$_2$—CH(CH$_3$)— | H | H | HO | H | Me | H | H | C$_{17}$H$_{16}$FN$_3$O$_4$S |
| 81 | C—O—CH$_2$—CH(CH$_3$)— | H | H | H$_2$N | Me | H | H | H | C$_{17}$H$_{17}$FN$_4$O$_3$S |
| 82 | C—O—CH$_2$—CH(CH$_3$)— | H | H | MeNH | Me | H | H | H | C$_{18}$H$_{19}$FN$_4$O$_3$S |
| 83 | C—O—CH$_2$—CH(CH$_3$)— | H | H | Me$_2$N | Me | H | H | H | C$_{19}$H$_{21}$FN$_4$O$_3$S |
| 84 | C—O—CH$_2$—CH(CH$_3$)— | H | H | HO | Me | H | H | H | C$_{17}$H$_{16}$FN$_3$O$_4$S |
| 85 | C—O—CH$_2$—CH(CH$_3$)— | H | Me | H$_2$N | H | Me | H | H | C$_{18}$H$_{19}$FN$_4$O$_3$S |
| 86 | C—O—CH$_2$—CH(CH$_3$)— | H | Me | MeNH | H | Me | H | H | C$_{19}$H$_{21}$FN$_4$O$_3$S |
| 87 | C—O—CH$_2$—CH(CH$_3$)— | H | Me | Me$_2$N | H | Me | H | H | C$_{20}$H$_{23}$FN$_4$O$_3$S |
| 88 | C—O—CH$_2$—CH(CH$_3$)— | H | Me | HO | H | Me | H | H | C$_{18}$H$_{18}$FN$_3$O$_4$S |
| 89 | C—O—CH$_2$—CH(CH$_3$)— | H | Me | H$_2$N | Me | H | H | H | C$_{18}$H$_{19}$FN$_4$O$_3$S |
| 90 | C—O—CH$_2$—CH(CH$_3$)— | H | Me | MeNH | Me | H | H | H | C$_{19}$H$_{21}$FN$_4$O$_3$S |
| 91 | C—O—CH$_2$—CH(CH$_3$)— | H | Me | Me$_2$N | Me | H | H | H | C$_{20}$H$_{23}$FN$_4$O$_3$S |
| 92 | C—O—CH$_2$—CH(CH$_3$)— | H | Me | HO | Me | H | H | H | C$_{18}$H$_{18}$FN$_3$O$_4$S |
| 93 | C—O—CH$_2$—CH(CH$_3$)— | H | H | H$_2$NCH$_2$ | H | H | H | H | C$_{17}$H$_{17}$FN$_4$O$_3$S |
| 94 | C—O—CH$_2$—CH(CH$_3$)— | H | H | EtNHCH$_2$ | H | H | H | H | C$_{19}$H$_{22}$FN$_4$O$_3$S |
| 95 | C—O—CH$_2$—CH(CH$_3$)— | H | H | H$_2$NCH$_2$ | Me | H | H | H | C$_{18}$H$_{19}$FN$_4$O$_3$S |
| 96 | C—O—CH$_2$—CH(CH$_3$)— | H | H | H$_2$NCH$_2$ | H | Me | H | H | C$_{18}$H$_{19}$FN$_4$O$_3$S |

Biological activity

The antimicrobial pharmacological activity of these compounds was studied according to the references indicated below.

Antimicrobial pharmacological activity (G. L. Daquet and Y. A. Chabbect, Techniques en bacteriologie, (Techniques in Bacteriology), Vol 3, Flammarion Médecine-Sciences, Paris 1972, and W. B. Hugo and A. D. Rusell, Pharmaceutical Microbiology, Blackwell Scientific Publications, London, 1977.

Culture medium and solvent:
 Antibiotic Agar No. 1 (Oxoid CM 327)
 Tryptone Soya Broth (Oxoid CM 129)
 Ringer physiological solution 1/4 (Oxoid BR 52)
 Dextrose Agar (BBL 11165)

Microorganisms:
 "Bacillus subtilis" ATCC 6633
 "Citrobacter freundii" ATCC 112606
 "Enterobacter aerogenes" ATCC 15038
 "Enterobacter cloacae" ATCC 23355
 "Bacillus cereus" ATCC 1178
 "Escherichia coli" ATCC 10799
 "Escherichia coli" ATCC 23559
 "Klebsiella pneumoniae" ATCC 10031
 "Proteus vulgaris" ATCC 8427
 "Morg. morganii" ATCC 8019
 "Pseudomonas aeruginosa" ATCC 9721
 "Pseudomonas aeruginosa" ATCC 10145
 "Salmonella typhimurium" ATCC 14028
 "Salmonella typhimurium" ATCC 6539
 "Serratia marcescens" ATCC 13880
 "Shigella flexnerii" ATCC 12022
 "Staphylococcus epidermis" ATCC 155-1
 "Staphylococcus aureus" ATCC 25178
 "Streptococcus faecalis" ATCC 10541

Preparation of the inocula.

Each of the microorganisms is seeded by streaking in tubes of antibiotic Agar No. 1 and incubated for 20 hours at 37° C. A culture loop is then taken, seeding is performed in Tryptone Soya Broth and the culture is incubated for 20 hours at 37° C. The culture obtained is diluted 4-fold with Ringer's physiological solution so as to obtain a standardized suspension of $10^{-10}$ cfu/ml for each organism.

Preparation of the medium containing the derivatives of general formula I.

Starting with a solution of 100 μg/ml, each product is diluted in Dextrose Agar (melted beforehand and maintained at 50° C.) by successive dilutions so as to obtain the following concentrations: 64, 32, 16, 8, 4, 2, 1, 0.5, 0.25 and 0.125 μg of derivative/ml of medium.

Each concentration of each product is subsequently distributed in Petri dishes 10 cm in diameter, on the basis of 10 ml of medium per dish and the same number of dishes as microorganisms to be tested.

When the medium has cooled, the dishes are seeded with the inocula on the basis of 0.4 ml of inoculum per dish. They are spread with a Driglasky loop and the supernatant is collected. The seeded dishes are incubated at 37° C. for 20 hours.

The results obtained are described in the following tables. The activity of the compounds "in vitro" is compared therein to that of norfloxacin. The concentrations are given in μg/ml.

TABLE II

| MICROORGANISM | Norfloxacin | EXAMPLES | | | | | | | | |
| --- | --- | --- | --- | --- | --- | --- | --- | --- | --- | --- |
| | | 1 | 3 | 2 | 5 | 9 | 10 | 22 | 29 | 33 |
| Bacillus subtilis ATCC 6633 | 0.25 | ≦0.03 | ≦0.03 | 0.03 | ≦0.03 | ≦0.03 | 0.03 | 0.03 | 0.06 | 0.12 |
| Bacillus cereus ATCC 11778 | 1.0 | 0.06 | 0.12 | 0.12 | ≦0.03 | ≦0.03 | 0.06 | 0.25 | 0.06 | 0.25 |
| Strep. faecalis ATCC 10541 | 1.0 | 0.12 | 0.50 | 0.25 | 0.25 | 0.12 | 0.06 | 0.50 | 0.25 | 0.50 |
| Staph. aureus ATCC 25178 | 2.0 | 0.06 | 0.06 | 0.12 | 0.06 | 0.06 | 0.06 | 0.06 | 0.12 | 0.25 |
| Staph. epidermidis ATCC 155-1 | 1.0 | ≦0.03 | 0.06 | 0.12 | 0.06 | ≦0.03 | 0.06 | 0.06 | 0.12 | 0.25 |
| PS. aeruginosa ATCC 9721 | 0.5 | 0.12 | 1.0 | 0.25 | 0.25 | 0.12 | 0.50 | 0.50 | 1.0 | 1.0 |
| PS. aeruginosa ATCC 10145 | 1.0 | 0.12 | 0.5 | 0.50 | 0.25 | 0.12 | 0.50 | 0.50 | 1.0 | 2.0 |
| Citr. freundii ATCC 11606 | 0.25 | ≦0.03 | 0.06 | 0.06 | ≦0.03 | ≦0.03 | 0.06 | 0.12 | 0.06 | 0.12 |
| Morg. morganii ATCC 8019 | 0.12 | ≦0.03 | 0.12 | 0.06 | ≦0.03 | ≦0.03 | 0.06 | 0.06 | 0.06 | 0.12 |
| Proteus vulgaris ATCC 8427 | 0.06 | 0.06 | 0.12 | 0.12 | 0.06 | 0.06 | 0.12 | 0.12 | 0.12 | 0.25 |
| Kleb. pneumoniae ATCC 10031 | 0.03 | ≦0.03 | 0.12 | 0.12 | ≦0.03 | ≦0.03 | 0.03 | 0.03 | 0.03 | 0.12 |
| Sal. typhimurium ATCC 14028 | 0.25 | 0.06 | 0.25 | 0.12 | ≦0.03 | ≦0.03 | 0.25 | 0.06 | 0.06 | 0.25 |
| Sal. typhi ATCC 6539 | 0.06 | ≦0.03 | 0.06 | 0.12 | ≦0.03 | ≦0.03 | 0.25 | 0.03 | 0.03 | 0.12 |
| Escherichia coli ATCC 10799 | 0.25 | ≦0.03 | 0.12 | 0.06 | ≦0.03 | ≦0.03 | 0.06 | 0.06 | 0.12 | 0.25 |
| Escherichia coli ATCC 23559 | 0.06 | ≦0.03 | ≦0.03 | 0.03 | ≦0.03 | ≦0.03 | 0.03 | 0.03 | 0.06 | 0.12 |
| Ent. aerogenes ATCC 15038 | 0.25 | ≦0.03 | 0.12 | 0.06 | ≦0.03 | ≦0.03 | 0.06 | 0.03 | 0.12 | 0.25 |
| Ent. cloacae ATCC 23355 | 0.06 | ≦0.03 | 0.12 | 0.12 | ≦0.03 | ≦0.03 | 0.06 | 0.03 | 0.03 | 0.12 |
| Serr. marcascens ATCC 13880 | 0.50 | ≦0.03 | 0.50 | 0.12 | 0.12 | 0.06 | 0.25 | 0.12 | 0.25 | 0.25 |
| Shigella flexnerii ATCC 12022 | 0.12 | ≦0.03 | ≦0.03 | 0.06 | ≦0.03 | ≦0.03 | 0.03 | 0.03 | 0.03 | 0.12 |

In human therapy, the dose for administration is naturally dependent on the susceptibility of the infective strain, the nature of the compound administered and the administration route. It will generally be between approximately 0.200 and approximately 300 mg per kilogram of body weight and per day. The derivatives of the invention will, for example, be administered in the form of tablets, solutions or suspensions, or alternatively gelatin capsules.

By way of examples, two particular dosage forms of the derivatives which are the subject of the present invention are shown below.

Example of formula per tablet:

| Example of formula per tablet: | |
| --- | --- |
| Compound of Example 5 | 50 mg |
| Microcrystalline cellulose | 100 mg |
| Povidone | 15 mg |
| Wheat starch | 73 mg |
| Colloidal silica | 50 mg |
| Magnesium stearate | 3 mg |
| Tablet weight | 300 mg |

Example of formula per gelatin capsule:

| -continued | |
| --- | --- |
| Compound of Example 5 | 100 mg |
| Polyoxyethylenated glyceride | 185 mg |
| Glyceryl behenate | 15 mg |
| Excipient: soft gelatin q.s. | 300 mg |

We claim:

1. A compound corresponding to the formula I:

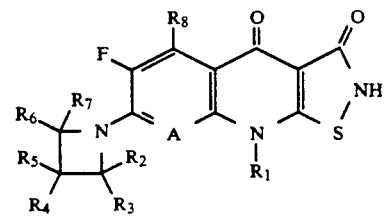

which may be written in its tautomeric formula II,

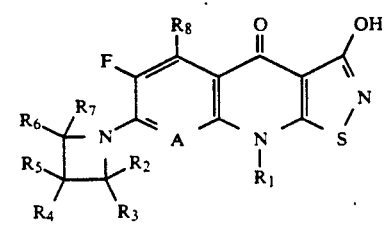

in which formulae A represents a nitrogen atom, or alternatively a carbon atom with a hydrogen atom attached (C—H), or alternatively a carbon atom with a halogen attached (C—X), and in this case X represents a bromine, chlorine or fluorine atom, $R_1$ represents a lower alkyl or cycloalkyl radical, a lower haloalkyl radical or an aryl radical, $R_2$ and $R_7$, which may be the same or different, represent a hydrogen atom or a lower alkyl radical, $R_3$, $R_5$, and $R_6$, which may be the same or different, represent a hydrogen atom, a lower alkyl radical, an aminoalkyl radical, an alkylamino radical or an alkyl-aminoalkyl radical, $R_4$ represents a hydrogen atom, a lower alkyl radical, a hydroxyl radical, an amino radical, an aminoalkyl radical, an alkylamino radical, a dialkylamino radical, an alkylaminoalkyl radical, an alkylcarboxamido radical, and it being possible in this case for the alkyl radical to be substituted with one or more halogens, an arylsulfonyloxyl radical, an alkylsulfonyloxy radical, a carboxamido radical, or a cyano radical, $R_8$ represents a hydrogen atom, a nitro radical or an amino or substituted amino radical, A and $R_1$ together can form a link represented by a group C—CH$_2$—CH$_2$—CHR$_9$— or C—O—CH$_2$—CHR$_9$— in which groups $R_9$ represents a hydrogen atom or a lower alkyl radical, and in the latter case a chiral centre with an "R" or "S" configuration, and its physiologically acceptable salts with inorganic acids, or with organic acids.

2. The compound corresponding to the formula I as claimed in claim 1, in which $R_1$ represents cyclopropyl; A represents a nitrogen atom, or alternatively a carbon atom with a hydrogen atom attached (C—H), or alternatively a carbon atom with a chlorine atom (C—Cl) or fluorine atom (C—F) attached; $R_2$, $R_7$, and $R_8$ represent a hydrogen atom; $R_3$, $R_5$ and $R_6$, which may be tho same or different, are selected from a hydrogen atom or a lower alkyl radical; and $R_4$ is selected from a hydrogen atom, a hydroxyl radical, an amino radical, an aminoalkyl radical, an alkylamino radical, a dialkylamino radical or an alkylaminoalkyl radical.

3. The compound corresponding to the formula I as claimed in claim 1, in which A and $R_1$ together form a link represented by a —C—C—CH$_2$—CH(CH$_3$)— group; $R_2$,$R_7$ and $R_8$ represent a hydrogen atom; $R_3$, $R_5$ and $R_6$, which may be the same or different, are selected from a hydrogen atom or a lower alkyl radical; and $R_4$ is selected from a hydrogen atom, a hydroxyl radical, an amino radical, an aminoalkyl radical, an alkylamino radical, a dialkylamino radical or an alkylaminoalkyl radical.

4. The compound corresponding to the formula I as claimed in claims 1, 2 or 3, selected from the following group:

9-cyclopropyl-6-fluoro-7-(3-amino-1-azetidinyl)-2,3,4,9-tetrahydroisothiazolo[5,4-b]quinoline-3,4-dione 9-cyclopropyl-6-fluoro-7-(3-methylamino-1-azetidinyl)-2,3,4,9-tetrahydroisothiazolo[5,4-b]quinoline-3,4-dione 9-cyclopropyl-6-fluoro-7-(3-dimethylamino-1-azetidinyl)-2,3,4,9-tetrahydroisothiazolo[5,4-b]quinoline-3,4-dione 9-cyclopropyl-6-fluoro-7-(trans-3-amino-2-methyl-1-azetidinyl)-2,3,4,9-tetrahydroisothiazolo[5,4-b]quinoline-3,4-dione 9-cyclopropyl-6-fluoro-7-(3-amino-3-methyl-1-azetidinyl)-2,3,4,9-tetrahydroisothiazolo[5,4-b]quinoline-3,4-dione 9-cyclopropyl-6-fluoro-7-(3-methylamino-3-methyl-1-azetidinyl)-2,3,4,9-tetrahydroisothiazolo[5,4-b]quinoline-3,4-dione 9-cyclopropyl-6-fluoro-7-(3-ethylamino-1-azetidinyl)-2,3,4,9-tetrahydroisothiazolo[5,4-b]quinoline-3,4-dione 9-cyclopropyl-6,8-fluoro-7-(trans-3-amino-2-methyl-1-azetidinyl)-2,3,4,9-tetrahydroisothiazolo[5,4-b]quinoline-3,4-dione 9-cyclopropyl-6,8-fluoro-7-(3-amino-3-methyl-1-azetidinyl)-2,3,4,9-tetrahydroisothiazolo[5,4-b]quinoline-3,4-dione.

5. A process for preparing the compound as claimed in any of claims 1, 2 or 3, which comprises the reaction of a compound of formula III

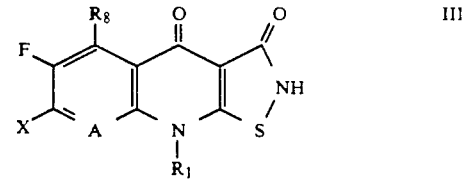

in which A, $R_1$, and $R_8$ have the meaning stated in claim 1 and X represents a halogen atom, preferably a chlorine or a fluorine,
with an azetidine of formula IV

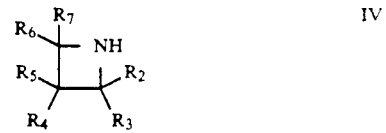

in which $R_2$, $R_3$, $R_4$, $R_5$, $R_6$ and $R_7$ have the meanings stated in claim 1, in which the reaction is performed in the presence of an organic solvent selected from the group consisting of dimethyl sulfoxide, dimethylformamide, pyridines, trialkylamines, methyl chloride, chloroform, ethers and mixtures thereof.

6. The process as claimed in claim 5, in which the reaction temperatures vary between room temperature and the refluxing temperature of the solvent, and the reaction time is between 1 hour and 24 hours.

7. A pharmaceutical composition, which contains, in addition to a pharmaceutically acceptable vehicle, an antimicrobially effective amount of at least one derivative of formula I or one of its physiologically acceptable salts, as claimed in one of clams 1, 2 or 3.

8. A method of treating microbial infections that comprise administering to a host a therapeutically effective amount of a compound of claims 1, 2, or 3, or a pharmaceutically acceptable acid addition salt thereof.

9. The compound of claim 1 wherein said aryl radical at the $R_1$ position is fluorine-substituted.

10. The compound of claim 1 wherein said physiologically acceptable salts are hydrochlorides.

11. The compound of claim 1 wherein said physiologically acceptable salts are toluenesulfonates or methylsulfonates.

12. The method of claim 5 wherein said ethers are selected from the group consisting of tetrahydrofuran and dioxane.

* * * * *

UNITED STATES PATENT AND TRADEMARK OFFICE
CERTIFICATE OF CORRECTION

PATENT NO. : 5,087,621            Page 1 of 2

DATED : February 11, 1992

INVENTOR(S) : Pinol et al.

It is certified that error appears in the above-indentified patent and that said Letters Patent is hereby corrected as shown below:

Column 3, line 36, delete [of9] and insert —of 9—.

Column 4, line 58, delete [of9] and insert —of 9—.

Column 4, line 61, delete [cyclopropyl6,] and insert —cyclopropyl 6,—.

Column 5, line 38, delete [point 300°] and insert —point > 300°—.

Column 6, line 2, delete [propyl6,] and insert —propyl 6,—.

Column 6, line 4, delete [methyl3-] and insert —methyl 3- —.

Column 6, line 4, delete [dihydrochldoride] and insert —dihydrochloride—.

Column 19, lines 27-28, delete [CH-$_2$] and insert —CH$_2$—.

Column 19, line 40, delete [tho] and insert —the—.

Column 20, line 12, delete [fluoro] and insert —difluoro—.

Column 20, line 15, delete [fluoro] and insert —difluoro—.

Table 1, Ex. 2, delete [NeNH] and insert —MeNH—.

Table 1, Ex. 16, delete [$C_{16}H_{18}FN_3O_3S$] and insert —$C_{18}H_{18}FN_3O_3S$—.

Table 1, Ex. 22, delete [$C_{19}H_{22}FN_4O_2S$] and insert —$C_{18}H_{20}FN_4O_2S$—.

UNITED STATES PATENT AND TRADEMARK OFFICE
CERTIFICATE OF CORRECTION

PATENT NO. : 5,087,621
DATED : February 11, 1992
INVENTOR(S) : Pinol et al.

It is certified that error appears in the above-indentified patent and that said Letters Patent is hereby corrected as shown below:

Table 1, Ex. 76, delete [$C_{16}H_{14}FN_3O_2S$] and insert --$C_{16}H_{14}FN_3O_4S$--.

Column 19, line 21, delete [arylsulfonyloxyl] and insert --arylsulfonyloxy--.

Signed and Sealed this

Second Day of July, 1996

Attest:

BRUCE LEHMAN

Attesting Officer

Commissioner of Patents and Trademarks